United States Patent [19]
Allen et al.

[11] Patent Number: 5,527,528
[45] Date of Patent: Jun. 18, 1996

[54] SOLID-TUMOR TREATMENT METHOD

[75] Inventors: Theresa M. Allen, Edmonton, Canada; Francis J. Martin, San Francisco, Calif.

[73] Assignee: Sequus Pharmaceuticals, Inc., Menlo Park, Calif.

[21] Appl. No.: 40,544

[22] Filed: Mar. 31, 1993

Related U.S. Application Data

[63] Continuation-in-part of Ser. No. 642,321, Jan. 15, 1991, Pat. No. 5,213,804, which is a continuation-in-part of Ser. No. 425,224, Oct. 20, 1989, Pat. No. 5,013,556.

[51] Int. Cl.$^6$ .......................... A61K 51/12; A61K 9/127; A61K 39/44
[52] U.S. Cl. .................. 424/178.1; 424/181.; 424/450; 424/812
[58] Field of Search ................... 424/85.8, 450, 424/181.1, 812, 178.1

[56] References Cited

U.S. PATENT DOCUMENTS

| | | | |
|---|---|---|---|
| 4,732,863 | 3/1988 | Tomasi et al. | 436/547 |
| 4,863,713 | 9/1989 | Goodwin et al. | 424/1.1 |
| 4,885,172 | 12/1989 | Bally et al. | 424/450 |
| 4,898,735 | 2/1990 | Barenholz et al. | |
| 4,948,590 | 8/1990 | Hawrot et al. | 424/450 |
| 5,013,556 | 5/1991 | Woodle et al. | 424/450 |

OTHER PUBLICATIONS

Ding, L., et al., "Effective drug–antibody targeting using a novel monoclonal antibody against the proliferative compartment of mammalian squamous carcinomas" *Cancer Immunol. Immunother.* 31: 105–109 (1990).

McQuarrie, S. A. et al., "A Pharmacokinetic Comparison of Murine and Chimeric Forms of the $^{99m}$Tc Labelled 174H.64 Monoclonal Antibody,"*JNM & Biol.*

Hnalowich et al., J. Nucl. Med. 28:1294, 1987, Investigations. . . Applications.

Abuchowski et al. J. Biol. Chem., 252:3582, Effect . . . Catalase, 1977.

Harris et al., TIBTECH, 1993, 11:42, Therapeutic. . . Age.

Zwierzina, Stem Cells, 1993, 11:144. Jansen, J. Biol. Chem. 1991, 266:3343.

Curti, Clin. Rev. Oncol. Hematol., 1993, 14:29. 271:58.

Galli; J. Nucl. Med. all. Sci., 1988, 32:110.

Jain, Sci. Amer, 1994, 271:58.

*Primary Examiner*—Margaret Parr
*Assistant Examiner*—F. Christopher Eisenschenk
*Attorney, Agent, or Firm*—Peter J. Dehlinger; Judy M. Mohr

[57] ABSTRACT

A method of administering an anti-tumor compound to a subject is disclosed. The method includes administering to a subject liposomes having sizes predominantly in the range 0.05 to 0.12 microns, and containing an anti-tumor compound in liposome-entrapped form, a surface coating of polyethylene glycol chains, at a surface concentration thereof sufficient to extend the blood circulation time of the liposomes severalfold over that of liposomes in the absence of such coating, and surface-attached antibody molecules effective to bind specifically to tumor-associated antigens present at the tumor site. One liposome composition includes doxorubicin in entrapped form, and, on the liposome surface, a monoclonal antibody against highly proliferating cells in a lung squamous cell carcinoma.

2 Claims, 6 Drawing Sheets

SOLID-TUMOR TREATMENT METHOD

This application is a continuation-in-part of application Ser. No. 642,321, filed Jan. 15, 1991, now U.S. Pat. No. 5,213,804, which in turn is a continuation-in-part of U.S. Ser. No. 425,224, now U.S. Pat. No. 5,013,556, filed Oct. 20, 1989.

FIELD OF THE INVENTION

The present invention relates to a method of treating a tumor, and in particular, to such a method employing long-circulation liposomes.

REFERENCES

Burrows, F. J., et al., (1992) *Cancer Res.* 52:5954–5962.

Kaneko, T., and LePage, G. A., (1978) *Cancer Res.* 38:2084–2090.

Mabrey, S., et al., (1978) *Biochem.* 17:2464–2468.

Mayer, L. D., et al., (1986) *Biochim. Biophys. Acta* 857:123–126.

Mayer, L. D., et al., (1989) *Canc. Res.* 49:5922–5930.

Martin, F. J. (1990) In: *Specialized Drug Delivery Systems-Manufacturing and Production Technology*, (P. Tyle, ed.) Marcel Dekker, New York, pp. 267–316.

Nedelman, M. A., et al., (1993) *J. Nuc. Med.* 34:234–241.

Olson, F., et al., (1979) *Biochim. Biophys. Acta* 557:9–23.

Saba, T. M. (1970) *Arch. Intern. Med.* 126:1031–1052.

Salmon, S. E., and Sartorelli, A. C. (1987) In: *Basic and Clinical Pharmacology* (ed. Katzung, B. G.), Appleton & Lange, pp. 665–701.

Samuel, J., et al., (1989) *Cancer Res.* 49:2465–2470.

Schmid, U., et al., (1993) *Eur. J. of Cancer* 29A:217–225.

Slavin-Chiorini, D. C., et al., (1993) *Int. J. of Cancer* 53:97–103.

Szoka, F., Jr., et al. (1980) *Ann. Rev. Biophys. Bioeng.* 9:467.

Tsong, T. Y. (1975) *Biochem.* 14:5409–5414, 5415–5417.

BACKGROUND OF THE INVENTION

Uncontrolled cell proliferation is a characteristic of a number of disease states. Such growth is observed, for example, in benign and malignant tumors. Generally, drugs used to treat cellular abnormalities characterized by uncontrolled cell growth target important biochemical steps or processes that are part of the cell growth cycle.

However, such drugs lack selectivity and affect both healthy and diseased cells. For example, numerous drugs currently used for treatment of hyperproliferative diseases are hepatotoxic above a threshold concentration (Saba). Certain antitumor drugs which inhibit growth of highly replicating cells may adversely inhibit the growth of cells in the bone marrow which also contains highly replicating cells (Salmon).

It would therefore be advantageous to have available a method for controlled, prolonged release of a drug in the bloodstream at a selected tumor site.

SUMMARY OF THE INVENTION

An object of the present invention is to provide a method of administering an anti-tumor compound to a subject. The method includes, in one aspect, administering to the subject, by parenteral injection, liposomes containing an anti-tumor compound in liposome-entrapped form, a surface coating of polyethylene glycol chains, at a surface concentration thereof sufficient to extend the blood circulation time of the liposomes severalfold over that of liposomes in the absence of such coating, and surface-attached antibody molecules effective to bind to tumor-associated antigens present at a tumor site. The liposomes have sizes preferably in the range 0.05 to 0.3 microns, and for targeting to a solid tumor, have sizes preferably in a selected size range between 0.05 to 0.12 microns.

The method substantially increases the therapeutic effect of the compound compared to that achievable by administering the same liposomes, but in the absence of the surface-attached antibody molecules.

In one embodiment the antibody molecules are biotinylated antibody molecules which are bound to the liposome surface by surface-bound avidin molecules.

In another embodiment the antibody molecules are coupled to the liposome surface by polyethylene glycol chains containing at their free ends a functionalized reactive group to which the antibody molecules are covalently attached.

In another aspect, the method includes administering to a subject for treatment of a solid-tumor, by parenteral injection, antibody molecules (i) effective to bind specifically to tumor-associated antigens, and (ii) having attached ligand molecules. After a 24–48 hour period to allow the antibody molecules to localize at the site of the solid tumor, liposomes are administered to the subject, by parenteral injection.

These liposomes have selected sizes in the size range 0.05 to 0.12 microns, and contain surface-bound anti-ligand molecules, an anti-tumor compound in liposome-entrapped form, and a surface coating of polyethylene glycol chains, at a surface concentration thereof sufficient to extend the blood circulation time of the liposomes severalfold over that of liposomes in the absence of such coating, thereby to localize the liposomes at the site of the solid tumor.

In one embodiment, the ligand molecules are biotin molecules, and the anti-ligand molecules are avidin molecules.

The method may also include, following the localization of the antibodies at the site of the solid-tumor, and prior to liposome administration, administration of a multivalent species capable of binding multiple antibodies with attached ligand molecules, to accelerate clearance of such nonspecifically-bound antibodies from the bloodstream.

In one embodiment, the ligand molecules are biotin molecules, and the multivalent species is a liposome with surface-attached avidin molecules.

The antibody molecule used to illustrate the present invention is a monoclonal antibody which binds to an antigen on highly proliferating cells in lung squamous carcinoma.

These and other objects and features of the invention will become more fully apparent when the following detailed description is read in conjunction with the accompanying figures and examples.

DETAILED DESCRIPTION OF THE INVENTION

The present invention provides a method for administering an anti-tumor compound to a subject by parenterally administering to the subject liposomes with an extended blood circulation time containing a liposome-entrapped drug. The liposomes may have, bound to the liposome surface, an antibody for specific targeting to tumor cells. Alternatively, the liposomes may have surface-bound avidin molecules for binding biotinylated antibodies bound in vivo to tumor-associated antigens.

More generally, the invention provides a method for targeting liposomes with an extended bloodstream circulation time to a site to obtain greater therapeutic activity of a liposome-entrapped compound at the site.

I. Definitions

The following terms, as used herein, have the meanings as indicated:

"Avidin" refers to both avidin, and the non-glycosylated form of avidin, strepavidin.

"Tumor-associated antigens" refers to antigens that are expressed at higher levels in tumor tissue relative to healthy tissue. The term also refers to antigens expressed uniquely in tumor tissue.

"Ligand molecules" refer to molecules attached to an antibody which have a high binding affinity for another molecule, referred to as an anti-ligand molecule, with an affinity constant greater than $10^6$ M$^{-1}$, and preferably greater than $10^9$ M$^{-1}$. "Anti-ligand molecules" refer to molecules attached to the surface of a liposome capable of binding the ligand molecules, as described. An example of such high-affinity binding between ligand and anti-ligand molecule, includes binding of biotin to avidin.

II. Antibody-Liposome Compositions

Figure 1A:
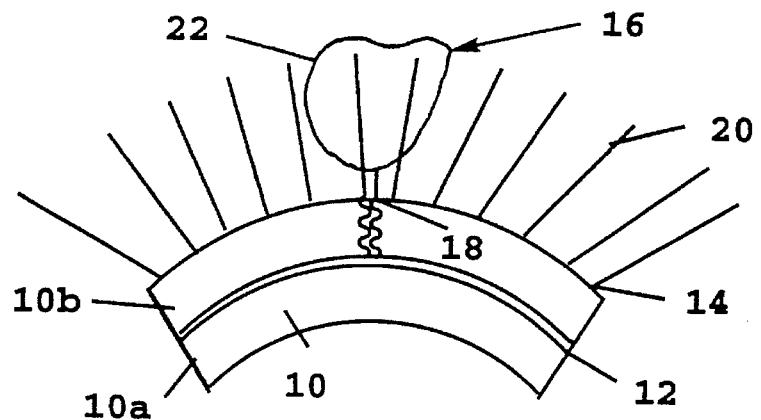
FIGS. 1A–1C are representations of antibody-liposome compositions, in which (a) an antibody molecule is directly attached to a liposome surface (FIG. 1A), (b) an antibody molecule is attached to a liposome surface by a polyethylene glycol (PEG) chain with a functionalized reactive end group (FIG. 1B), and (c) an antibody molecule is bound by biotin/avidin coupling to a liposome having surface-bound biotin moieties (FIG. 1C)
Figure 1B:
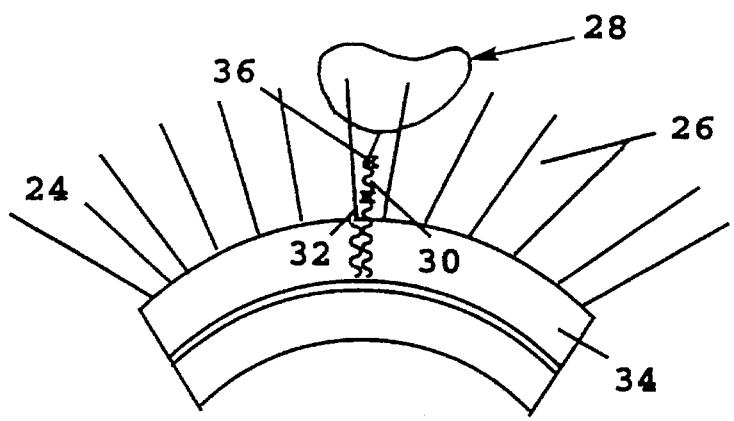
Figure 1C:
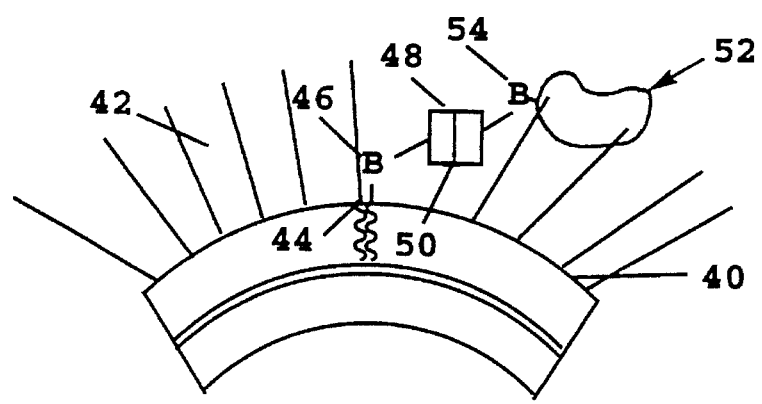

FIGS. 1A–1C illustrate various embodiments of a antibody-liposome composition for use in the invention. The composition will be described in its general features with respect to FIG. 1A. The figure shows a portion of the outer bilayer 10 of a liposome 12 having an outer surface 14. The liposome may include additional bilayers. The outer bilayer itself is composed of confronting lipid layers 10a and 10b which are the interior and exterior lipid layers, respectively, of the bilayer, each layer being composed of vesicle-forming lipids, such as phospholipids and cholesterol. Methods for forming liposomes suitable for use in the composition are described below. More generally, the liposome is representative of a particle support forming part of the composition.

The composition includes molecules of an antibody molecule, such as antibody 16, which is bound to the outer liposome surface by covalent or noncovalent coupling to one of the lipids, such as indicated at 18, forming the outer layer of the outer bilayer. Antibody molecules suitable for use in the invention, and methods of their preparation are described below. In the embodiment shown, the antibody is attached by direct covalent coupling to the polar head group of a lipid, such as lipid 18, in the outer layer of the liposome's outer bilayer.

In the embodiments discussed below, other methods of attaching antibodies to the outer surfaces of liposomes are described.

According to an important feature of the invention, the antibody molecules attached to the liposome outer surface are partially surrounded by, but not covalently linked to, hydrophilic polymer chains, such as chains 20, which are also carried on the liposome's outer surface. The polymer chains form a polymer layer about the liposome surface which allows the liposomes to circulate in the bloodstream over an extended period of time compared to liposomes lacking the polymer coating.

The antigen recognition region, such as antigen recognition region 22, of the antibody molecule is accessible for binding to antigens at a target site. The polymer coating on the liposome surface does not affect antigen-antibody interactions.

The polymer chains are preferably polyethylene glycol (PEG) chains having molecular weights between about 1,000 and 10,000 daltons, corresponding to polymer chain lengths of about 22 to 220 ethylene oxide units. The polymer chains are covalently attached to the polar head groups of vesicle-forming lipids as described in co-owned U.S. Pat. No. 5,013,556, herein incorporated by reference.

In one particular embodiment, illustrated in FIG. 1B, the antibody molecule in the composition is attached to the liposome outer surface by a polymer spacer chain. The figure shows a liposome bilayer portion 24 with a layer 26 of PEG chains, as above. The antibody, such as antibody 28, is attached to the liposome outer surface by a spacer chain, such as chain 30. The spacer chain is preferably a hydrophilic chain, such as a 100–5,000 dalton PEG chain, which is itself coupled to the polar head group of a lipid, such as lipid 32, in the outer layer 34 of the liposome bilayer. The spacer chain contains a reactive functionalized group 36 at its free end for coupling antibody.

The present embodiment allows the antibody in the polymer layer to be positioned at a selected depth in the layer, as shown, to increase or decrease the extent to which the antibody is buried in the polymer layer. For example, if the antibody is a xenogeneic antibody which elicits an immunogenic response the antibody is preferably buried to hide immunogenic sites while retaining the antigen recognition region accessible for binding to a target site. If the antibody is nonimmunogenic, the antibody can be localized on the outer surface coating of polyethylene glycol chains.

In another embodiment, illustrated in FIG. 1C, the antibody is a biotinylated antibody attached to the liposome outer surface by specific, high-affinity binding to avidin carried on the liposome outer surface. The avidin is bound noncovalently to the liposome outer surface by high-affinity interactions with biotin which has been used to derivatize lipid head groups on the liposome surface.

The figure shows a liposome bilayer portion 40 with a layer 42 of PEG chains, as above. The liposome outer surface contains a number of lipid polar head groups, such as lipid polar head group 44, which have been derivatized by biotin. To a biotin moiety on the liposome surface, such as biotin moiety 46, is bound an avidin molecule, such as avidin molecule 48. Each avidin molecule contains four high-affinity biotin binding sites, such as biotin binding site 50. To one or more of these sites is attached the liposome bound biotin as previously indicated. To one or more of the free-remaining sites can be bound a biotinylated antibody, such as biotinylated polypeptide 52, which is derivatized by a biotin molecule, such as biotin molecule 54.

Although the antibody-liposome composition of the invention has been described above with respect to one having a liposomal particle support, it will be recognized that a variety of other particles supports may be used. In general, the particle supports should be biodegradable, have surface chemical groups through which polymer chains of polypeptide molecules can be attached to the surface, and preferably have sizes in a selected size range between about 50–300 nm. Exemplary particle supports of this type include sized polylactic acid particles, or microcapsules formed of poly(amino acids).

A. Lipid Components

The liposomes of the present invention are generally composed of at least three types of lipid components. A first type, which will form the bulk of the liposome structure, includes any amphipathic lipids having hydrophobic and polar head group moieties, and which (a) can form spontaneously into bilayer vesicles in water, as exemplified by phospholipids, or (b) are stably incorporated into lipid bilayers, with its hydrophobic moiety in contact with the interior, hydrophobic region of the bilayer membrane, and its polar head group moiety oriented toward the exterior, polar surface of the membrane.

The vesicle-forming lipids of this type are preferably ones having two hydrocarbon chains, typically acyl chains, and a polar head group. Included in this class are the phospholipids, such as phosphatidylcholine (PC), PE, phosphatidic acid (PA), phosphatidylglycerol (PG), phosphatidylinositol (PI), and sphingomyelin (SM), where the two hydrocarbon chains are typically between about 14–22 carbon atoms in length, and have varying degrees of unsaturation. The above-described lipids and phospholipids whose acyl chains have a variety of degrees of saturation can be obtained commercially, or prepared according to published methods. Other lipids that can be included in the invention are glycolipids.

A second lipid component includes a vesicle-forming lipid which is derivatized with a polymer chain. The vesicle-forming lipids which can be used are any of those described above for the first vesicle-forming lipid component. Vesicle-forming lipids with diacyl chains, such as phospholipids, are preferred. One exemplary phospholipid is phosphatidylethanolamine (PE) with a reactive amino group which is convenient for coupling to the activated polymers. An exemplary PE is distearyl PE (DSPE).

The preferred polymer in the derivatized lipid, is polyethyleneglycol (PEG), preferably as a PEG chain having a molecular weight between 1,000–10,000 daltons, more preferably between 2,000 and 5,000 daltons. Once a liposome is formed, the polyethylene glycol chains provide a surface coating of hydrophilic chains sufficient to extend the blood circulation time of the liposomes in the absence of such a coating.

Other hydrophilic polymers which may be suitable include polyvinylpyrrolidone, polymethyloxazoline, polyethyloxazoline, polyhydroxypropyl methacrylamide, polymethacrylamide, polydimethylacrylamide, polylactic acid, polyglycolic acid, and derivatized celluloses, such as hydroxymethylcellulose or hydroxyethylcellulose. Lipid-polymer conjugates containing these polymers attached to a suitable lipid, such as PE, have been described in co-owned, co-pending U.S. patent application No. 08/025,602. This application is incorporated herein by reference.

A third type of lipid component are vesicle-forming lipids which have been modified for coupling antibody molecules to the liposome outer surface. These modified lipids may be of different types. In one embodiment, the modified lipid may contain a hydrophilic polymer spacer chain attached to the lipid. The hydrophilic polymer is typically end-functionalized for coupling antibody to its functionalized end. The functionalized end group is preferably a maleimide group for selective coupling to antibody sulfhydryl groups. Other functionalized end groups include bromoacetamide and disulfide groups for reaction with antibody sulfhydryl groups, activated ester and aldehyde groups for reaction with antibody amine groups. Hydrazide groups are reactive toward aldehydes, which can be generated on numerous biologically relevant compounds. Hydrazides can also be acylated by active esters or carbodiimide-activated carboxyl groups. Acyl azide groups reactive as acylating species can be easily obtained from hydrazides and permit the attachment of amino containing ligands.

A preferred polymer in the derivatized lipid, is polyethylene glycol (PEG). Other hydrophilic polymers which may be suitable for lipid derivatization include end-functionalized polyvinylpyrrolidone, polymethyloxazoline, polyethyloxazoline, polyhydroxypropyl methacrylamide, polymethacrylamide, polydimethylacrylamide, polylactic acid, polyglycolic acid, and derivatized celluloses, such as hydroxymethylcellulose or hydroxyethylcellulose.

This polymer spacer chain is preferably shorter than the polymer chain forming the liposome surface polymer coating layer. For example, in a liposome composition containing a layer formed by PEG polymers of 2,000–5,000 daltons, the spacer arm is generally of 100–5,000 daltons, preferably 600–4,000 daltons.

In another embodiment the phospholipid may be modified by a biotin molecule. To attach the antibody molecule to the biotinylated liposome surface, once the liposome is formed, the antibody molecule is also modified with biotin and then incubated in the presence of the avidin. Biotinylated lipids, such as biotinylated PE, are commercially available.

More generally, lipids may be modified by a substrate for use in binding a targeting molecule to a liposome surface. Typically, substrates, as exemplified with biotin, are relatively small, e.g., less than about 5,000 daltons, to allow their incorporation into multilamellar liposomes with a minimum of disruption of the lipid bilayer structures. The substrate is preferably one capable of binding irreversibly to a targeting molecule, to ensure that the targeting molecule remains bound to the liposomes over its lifetime in the bloodstream.

Additionally, the liposomes may include lipids that can stabilize a vesicle or liposome composed predominantly of phospholipids. The most frequently employed lipid from this group is cholesterol at between 25 to 40 mole percent. At between 0 to 20 mole percent cholesterol in a bilayer, separate domains exist containing cholesterol and phospholipids and pure phospholipid (Mabrey). These bilayers show an increased permeability to water (Tsong). At mole percentages above 50% cholesterol starts destabilizing the bilayer.

B. Liposome-entrapped Compound

A variety of therapeutically active compounds are suitable for delivery by the liposome composition. The compound is useful, preferably, for treatment of a tumor. More generally, the therapeutic compound in liposome-entrapped form is used to treat diseased cells accessible to liposome-entrapped compounds in the bloodstream.

One general class include water soluble, liposome permeable compounds which are characterized by a tendency to partition into the aqueous compartment of the liposome composition, and to equilibrate over time into the outer bulk phase of the liposome composition. Preferred drugs are those that have a low liposome permeability. Representative drugs of this kind include cytarabine, cyclophosphamide, methotrexate, gentamicin, and bleomycins, among others.

A second general class of compounds are those which are water-soluble, but liposome impermeable. These compounds include peptide or protein molecules, such as peptide hormones, enzymes, enzyme inhibitors, and higher molecular weight carbohydrates. Representative compounds include peptide hormones, such as vasopressin, cytokines, such as interferons (alpha, beta, gamma), interleukins, and colony stimulating factors (macrophage, granulocyte, granulocyte and macrophage), viral or bacterial vaccines, melanoma vaccine, streptokinase, or other anti-thrombolytic peptides, and superoxide dismutase.

A third class of drugs are lipophilic molecules that tend to partition into the lipid bilayer phase of the liposomes, and which are therefore associated with the liposomes predominantly in a membrane-entrapped form. The drugs in this class include adrenocorticosteroids, prostaglandins, amphotericin B, nitroglycerin, polymyxins, carmustine, dacarbazine, dexamethasone, daunomycin and doxorubicin.

The liposome-entrapped compound may also be an imaging agent for tracking progression of a disease, such as tumor metastasis. Imaging agents include chelates of radionuclides, such as technetium-99, indium-111, and iodine-124.

C. Antibody Molecules

The antibodies are monoclonal antibodies or antibody fragments which are used for targeting tumor-associated antigens in the treatment of cancer. These antibodies or antibody fragments are typically derived from hybridomas that show positive reactivity toward the tumor tissue and negative reactivity toward healthy tissue (Samuel).

Several monoclonal antibodies are known which react with tumor-associated antigens. For example, the antibody may be a monoclonal antibody that reacts with a high-molecular mucin expressed on several types of human carcinoma (Slavin-Chiorini). Alternatively, the antibody may be an antibody that targets an antigen of tumor vascular epithelium. This type of targeting may be applicable to many types of solid tumors since many tumors require a blood supply, and epithelial cells are readily accessible from the bloodstream (Burrows).

The liposomes can be used, for example, for targeting spontaneous liver metastases by use of an antibody that binds to an antigen expressed on metastasizing liver cells, but not on normal liver tissue (Schmid).

The antibodies may also be used to localize a liposome-entrapped compound at non-tumor cells. For example, the antibody may be used to target liposomes to sites of myocardial necrosis (Nedelman). Liposome entrapped compounds administered to these site may be superoxide dismutase or antithrombolytic compounds for treatment of symptoms associated with myocardial infarction. The antibody may also be used for targeting a virus or a bacterium, and the antibody recognizes an antigen associated with either virus or bacterium.

In experiments performed in support of the present invention, IgG$_1$ monoclonal antibodies, 174H.64 (mAb), were used to target a liposome-entrapped drug to lung tumor cells. These antibodies recognize a unique epitope on proliferating cells of murine lung squamous carcinoma, KLN-205, as well as of human and bovine squamous carcinoma (Samuel).

III. Antibody-Liposome Composition

This section describes the synthesis of some exemplary modified lipids for use in coupling antibody molecules to a liposome surface. Also described are methods of preparing liposomes which incorporate the modified lipids, and for coupling antibodies to a liposome surface via the modified lipids.

A. Modified Lipid Preparation

Figure 2A:
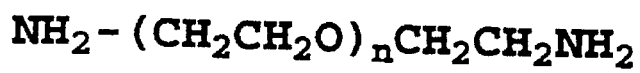
FIGS. 2A–2B show steps in forming a PE derivatized by a PEG spacer chain having a maleimide group at its free end.
Figure 2A:
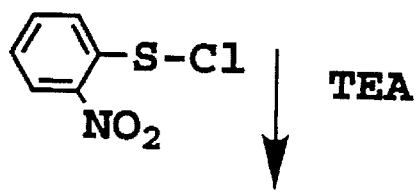
Figure 2A:
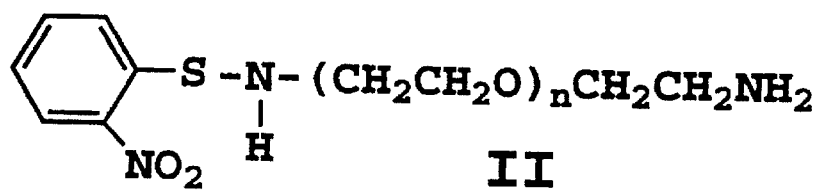
Figure 2A:
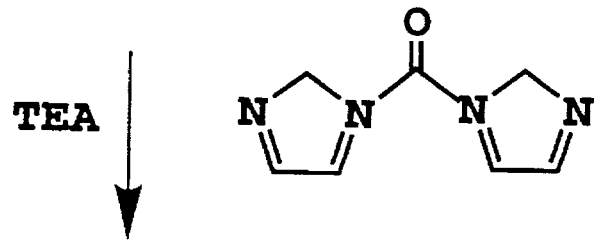
Figure 2B:
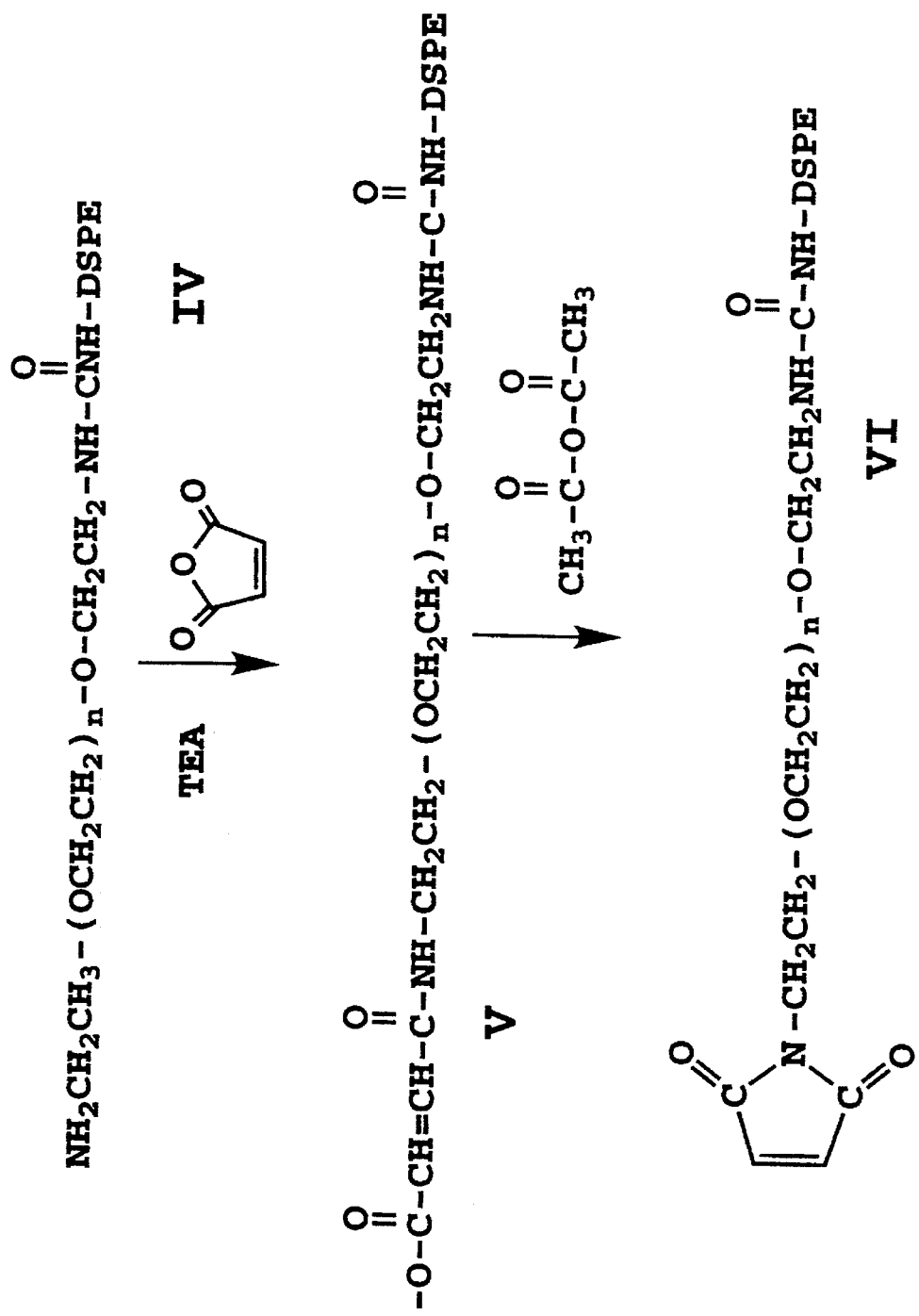

FIGS. 2A–2B show the synthesis of a DSPE derivatized with a PEG chain and having a maleimide group at the chain's free end. Initially, PEG bis (amine) (compound I), protected at one end by 2-nitrobenzene sulfonyl chloride (compound II), is reacted with carbonyl diimidazole in triethylamine (TEA) to form the imidazole carbamate of the mono 2-nitrobenzenesulfonamide (compound III). The compound is reacted with DSPE in TEA to form the derivatized PE lipid protected at one end with 2-nitrobenzyl sulfonyl chloride. The protective group is removed by treatment with acid to give the DSPE-PEG (compound IV) having a terminal amine on the PEG chain. Reaction with maleic acid anhydride gives the corresponding maleamic (compound V), which on reaction with acetic anhydride gives the PE-PEG-maleimide (compound VI). Details of the reactions are given in Example 1.

Alternatively, a DSPE derivatized with a PEG chain having a hydrazide group at the chain's free end may be synthesized. Details for the synthesis of such a DSPE derivative is described in co-owned, co-pending application for "Polymer-Polypeptide Composition and Method".

Figure 3:
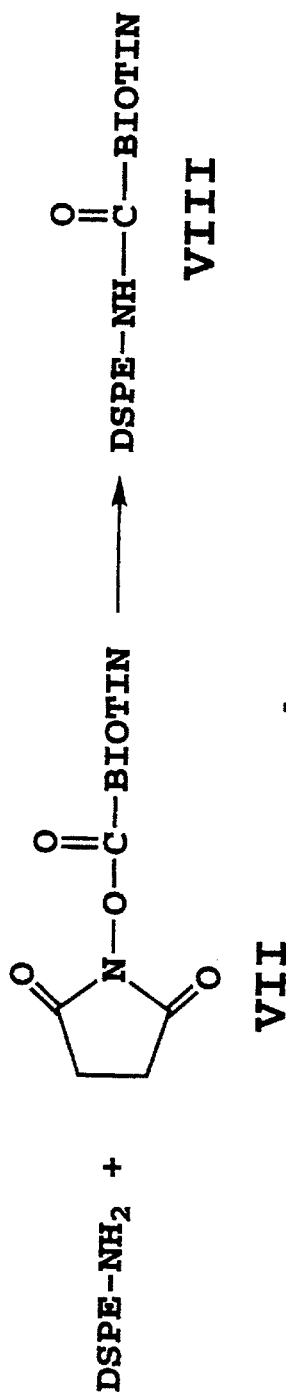
FIG. 3 illustrates the preparation of a biotinylated PE for use in preparing liposomes with surface-bound biotin.

FIG. 3 shows the synthesis of a DSPE derivatized with a succinimide ester of biotin (compound VII). The biotinylated phospholipid (compound VIII) is incorporated into liposomes. The liposomes are then incubated with avidin and biotinylated antibody as described in Example 2.

B. Liposome Preparation

The liposomes may be prepared by a variety of techniques, such as those detailed in Szoka et al, 1980. Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns. In an alternative method, liposomes are prepared by vortexing dried lipid films in a buffered aqueous solution (Olson).

Liposome compositions are typically prepared with lipid components present in a molar ratio of about 30–75 percent vesicle-forming lipids, 25–40 percent cholesterol, 1–20 percent polymer-derivatized lipid, and 0.01–10 mole percent of the lipid derivative employed for antibody coupling. One exemplary liposome formulation includes hydrogenated soy phosphatidylethanolamine (HSPE), cholesterol (CH), DSPE-PEG at a molar ratio of 2:1:0.1. The composition also includes 0.05 mole percent phosphatidylethanolamine derivatized with biotin (biotin-PE). Another exemplary liposome formulation includes hydrogenated soy phosphatidylethanolamine (HSPE), cholesterol (CH), and DSPE-PEG at a molar ratio of 2:1:0.1. The composition also includes 1 mole percent DSPE-PEG derivatized with hydrazide (DSPE-PEG HZ).

Generally, a therapeutic drug is incorporated into liposomes by adding the drug to the vesicle-forming lipids prior to liposome formation, as described below, to entrap the drug in the formed liposome. If the drug is hydrophobic the drug is added directly to the hydrophobic mixture. If the drug is hydrophilic the drug can be added to the aqueous medium which covers the thin film of evaporated lipids.

Alternatively, the drug may be incorporated into preformed liposomes by active transport mechanisms. Typically, in this case drug is taken up in liposomes in response to a potassium or hydrogen ion concentration differential (Mayer, 1986; Mayer, 1989).

One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin).

C. Antibody Coupling to Liposome Surface

Antibody may be attached to a liposome surface by covalent or noncovalent attachment methods as has been described. For attaching an antibody covalently to a liposome surface, a derivatized lipid containing an end-functionalized polyethylene glycol chain is incorporated into liposomes. After liposome formation, the end-functionalized group can react with an antibody for antibody coupling to a liposome surface.

Alternatively, an antibody-lipid derivative may be first formed and then incorporated into a liposome. As an example, an antibody is coupled to the maleimide group of a free DSPE-PEG molecule. The antibody-coupled DSPE-PEG molecule is then employed to form vesicles.

Figure 4:
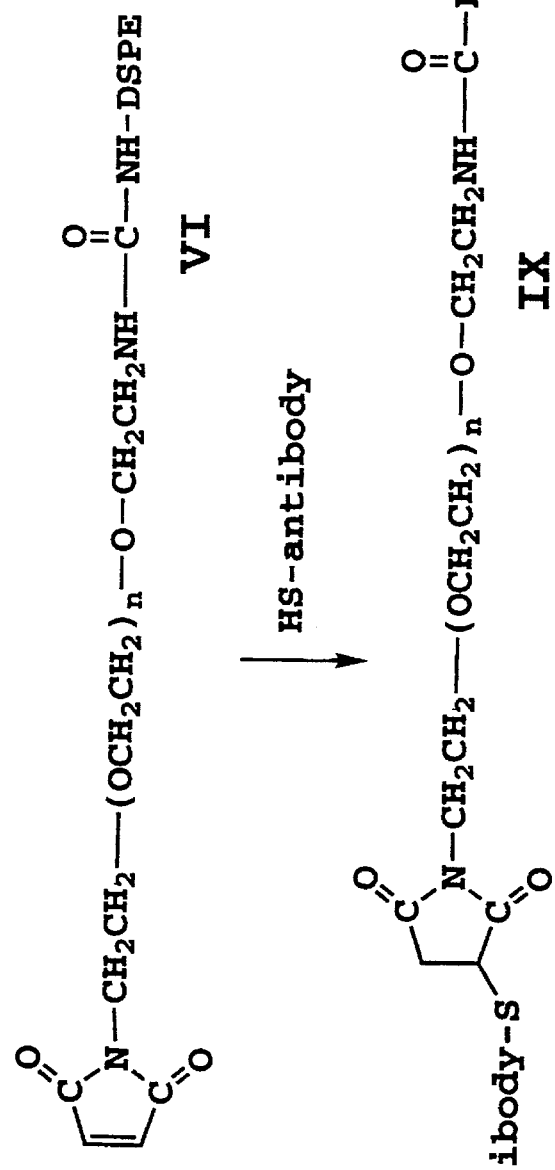
FIG. 4 shows the coupling of an antibody to PE derivatized by a PEG chain having a reactive maleimide group at its free end.

As illustrated in FIG. 4 the end-functionalized group is a maleimide group which is preferentially reactive with sulfhydryl groups. Antibodies contain sulfhydryl groups which react at the maleimide group forming a thioether linkage to generate compound IX. Details of the reactions are given in Example 1.

Alternatively, the polymer end-functionalized group is a hydrazide group. For antibody coupling to the liposome surface, antibody hydroxyl groups are oxidized to aldehydes by mild periodate oxidation. The periodate-treated protein is added to liposomes containing DSPE-PEG hydrazide and incubated overnight. Unbound antibodies are then separated from the antibody-liposomes by gel filtration. The procedure is described in Example 2.

Figure 5A:
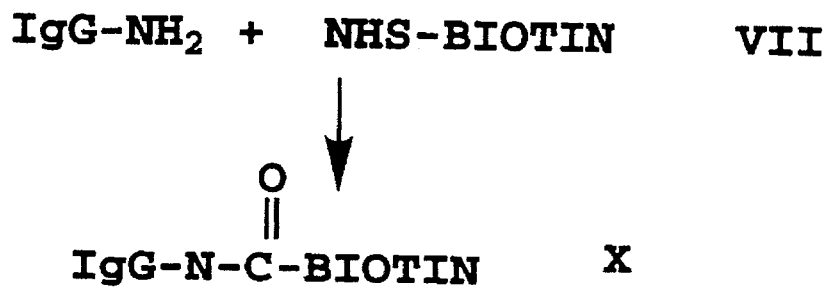
FIGS. 5A and 5B show the preparation of a biotinylated IgG (FIG. 5A), and binding of the biotinylated IgG molecule to a liposome surface containing biotinylated PE via high affinity interactions between surface-bound biotin, avidin, and biotin attached to IgG (FIG. 5B)
Figure 5B:
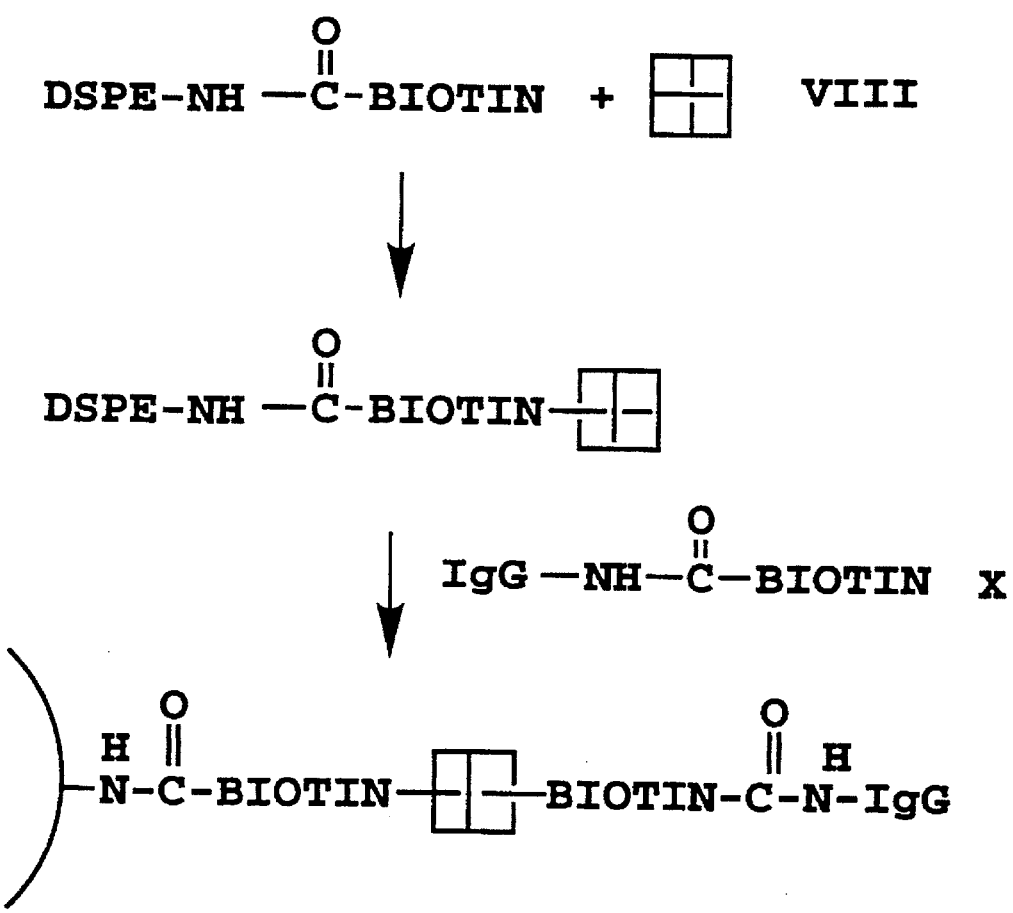

An exemplary method for attaching antibodies noncovalently to liposomes is illustrated in FIGS. 5A and 5B. FIG. 5A shows the preparation of a biotinylated monoclonal IgG antibody to generate compound X. FIG. 5B shows coupling of biotinylated antibody to the liposome surface by first binding avidin, represented in FIG. 5B as a rectangle divided into 4 parts, to the liposomes, then incubating the avidin-coated liposomes with the biotinylated antibody. Experiments conducted in support of the present invention indicate that antibodies are efficiently attached to PEG-coated liposomes by this method. Details are given in Example 3.

IV. Utility

According to an important aspect of the invention, it has been found that the antibody-liposome composition described is able to substantially increase the therapeutic effect of a compound entrapped in the liposomes, when measured against the same long-circulating liposomes, but in the absence of surface-attached antibodies. Studies showing this effect are described in Part A below. The greater therapeutic effect achievable leads to a more effective tumor treatment method, as described in Part B below.

A. Therapeutic Efficacy of Antibody-liposome Composition in vivo

Experiments were performed to investigate the half-life in the bloodstream and the tissue biodistribution of the antibody-liposome composition. For these experiments liposomes containing PEG end-functionalized with a hydrazide group covalently linked to sheep IgG were prepared as described in Example 2.

Other experiments to determine the blood circulation times of antibody-liposomes were performed using liposomes containing surface-bound avidin and biotinylated antibodies. Liposomes with surface-bound antibodies possessed long circulation times in the bloodstream similar to that of liposomes containing PEG derivatized lipids but lacking the surface-bound antibodies. Twenty-four hours post-injection 34.7±6.7% of mAb liposomes were in the blood. This level is comparable to that of liposomes containing PEG, but lacking the antibody (37.5±9.7% at 24 hours).

As shown in Table 1 the tissue biodistribution of liposomes containing antibody covalently attached to the end of a PEG chain by a hydrazide group is very similar to those of liposomes containing nonfunctionalized PEG chains. Liposome biodistribution was determined for the blood, liver, spleen, lung, heart and carcass.

Other experiments were performed to show increased therapeutic effect of the antibody-liposome composition in the treatment of tumor cells in vivo, compared to the same liposomes but lacking the attached antibody. An antibody-liposome composition was prepared, as described in Example 3, to contain on their outer surface $IgG_1$ monoclonal antibodies 174H.64 (mAb), which recognizes a unique epitope on proliferating cells of murine lung squamous carcinoma, KLN-205, as well as those for human and bovine squamous carcinoma. The liposomes were tested for their therapeutic effectiveness for treatment of KLN-205 carcinoma. The KLN-205 carcinoma lodges in the lung of DBA2 mice within 3 days following intravenous injection (Kaneko).

Figure 6:
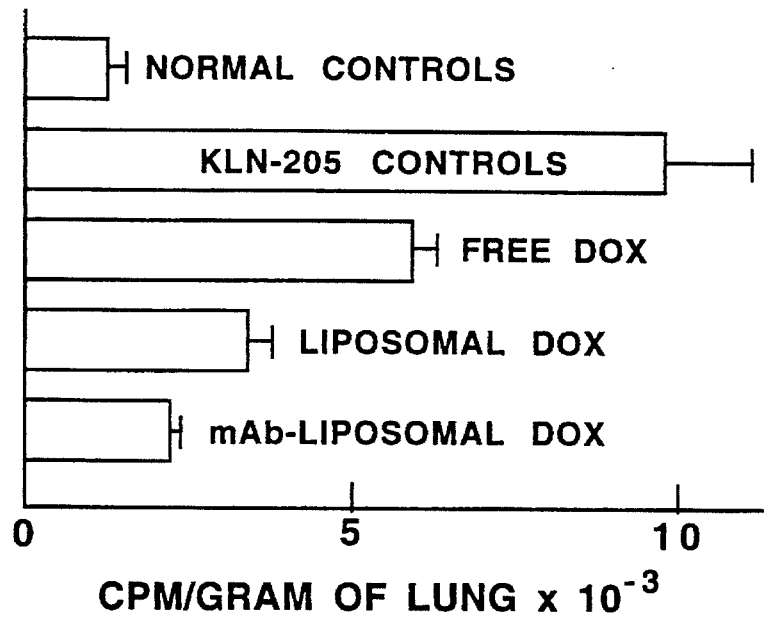
FIG. 6 shows $^{125}$dUrd uptake in normal and tumor-bearing DBA/2 mice (3/group) 45 days after i.v. injection of $2\times10^5$ KLN-205 cells.

FIG. 6 shows the growth inhibitory effect of doxorubicin intravenous injections as reflected by a decrease in deoxyuridine uptake by tumor cells in the lung. For these experiments mice were injected intravenously with KLN-205 cells. At three days post-injection the mice were treated by administering intravenously a single dose of doxorubicin (6 mg/kg body weight). Doxorubicin was administered in either free form (not encapsulated in liposomes) (DOX), encapsulated in liposomes lacking the antibody (liposomal DOX), or encapsulated in antibody-liposome compositions (mAb liposomal DOX).

The effect of doxorubicin administration on the viability of the cancerous cells was monitored by uridine uptake 45 days post-tumor injection as described in Example 4. Uridine uptake into lung has been established to be directly proportional to the number of intravenous injections of KLN-205 tumor cells in the range of $10^5$ to $10^6$ injected cells and reflects the number of highly proliferating cells in a tissue. Uridine uptake in lungs from normal mice in the absence of tumor is low.

A single injection of mAb-liposomal DOX resulted in an 80% reduction in the growth of lung tumors as measured by radiolabelled deoxyuridine uptake. Single injections of liposomal DOX resulted in a 65% reduction in the growth of the lung tumors. Administration of free doxorubicin resulted in only a 40% reduction in lung tumor growth.

To confirm the effectiveness of tumor suppression by the present invention histopathological studies were also performed as described in Example 5. These studies showed that the presence of tumor nodules was minimal after mAb-liposomal DOX administration. Animals that received single injections of liposomal DOX showed fewer nodules than those that received free DOX or no treatment.

The number of discrete tumor foci/linear cm of lung were counted for both the right and left lungs for 1 or 2 mice from each treatment group of 5 mice, and mean tumor diameters were determined as compiled in Table 2. The number of tumor foci/linear cm was negligible for mice receiving mAb-liposomal DOX.

Liposome uptake in the lung was also examined and is described in Example 6. Uptake of liposomes containing radiolabeled tyraminylinulin in mAb-liposome-entrapped form by tumor lung tissue was greater than for liposomes lacking antibody bound at the liposome surface.

The results obtained indicate that liposomes containing entrapped doxorubicin, lipids derivatized with PEG, such as PEG-DSPE, and containing an antibody on the liposomes' outer surface (mAb-liposomal DOX) are valuable for increasing the therapeutic effectiveness of doxorubicin administration to a site in a subject. The method of the present invention is likely applicable to the targeting of other therapeutic compounds to tumor sites, or other target sites.

B. Tumor-Treatment Method

In one embodiment of the invention, the above described antibody-liposome composition, containing an anti-tumor compound in liposome-entrapped form, is used for tumor treatment. The antibody-liposome likely enhances the therapeutic efficacy of the compound by localizing the liposome, and the anti-tumor compound, selectively at the tumor site.

Figure 7:
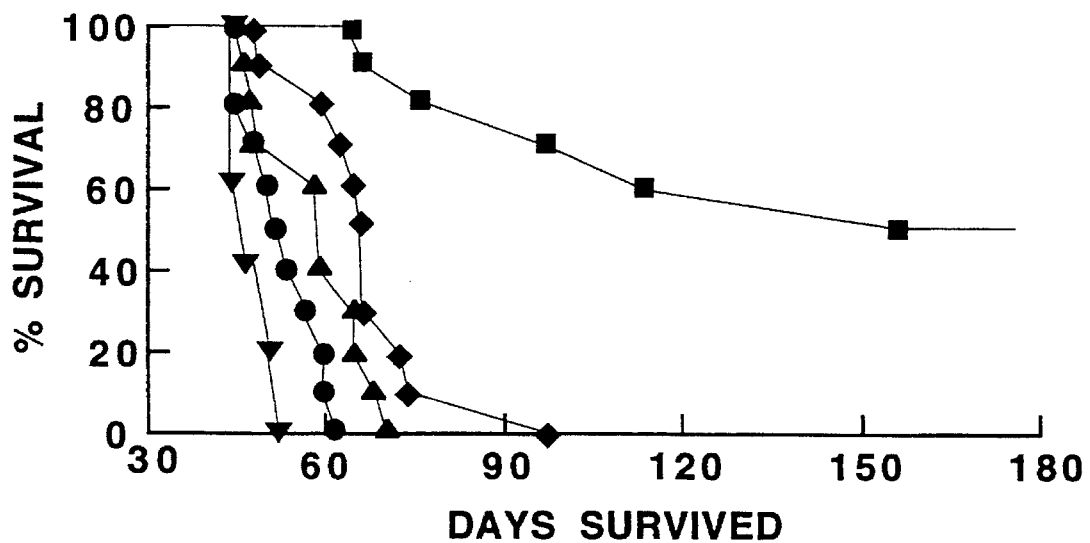
FIG. 7 shows survival times for DBA/2 mice inoculated i.v. with $2\times10^5$ KLN-205 cells and treated on the 3rd day with 6 mg/kg of either free DOX (▲), liposomal DOX (♦), mAb-liposomal DOX (■) or mAb-liposomes (▼) (12 μg mAb, no DOX), control groups (●) were treated with sterile PBS.

The ability to effectively treat solid tumors, in accordance with the present invention, has been shown in an in vivo lung squamous cell carcinoma model. Significantly, in this tumor model, doxorubicin administered parenterally in antibody-liposome entrapped form substantially increased the survival time of mice with lung tumor. FIG. 7 shows survival data for mice receiving various treatments of doxorubicin at doses of 6 mg/kg body weight, as described in Example 4. The mean survival time (MST) for mice treated with mAb liposomal DOX, that died from their tumors was 99.2±36.1 days and was substantially longer than the MST for untreated mice (52.0±5.8 days). The MST for liposomal DOX and free DOX was 65.8±13.1 days and 57.6±9.3 days, respectively. The group treated with doxorubicin in mAb-liposome entrapped form showed a 50% survival rate. The groups treated with either DOX, liposomal DOX, or which received no doxorubicin treatment had no long-term survivors.

The method of the present invention is of utility for the treatment of both "solid" tumors and blood-born tumors. A solid tumor is defined as one that grows in an anatomical site outside the bloodstream (in contrast, for example, to blood-born tumors such as leukemias) and requires the formation of small blood vessels and capillaries to supply nutrients, etc. to the growing tumor mass.

The anti-tumor compound which may be used is any compound, including the ones listed below, which can be stably entrapped in liposomes at a suitable loading factor and administered at a therapeutically effective dose (indicated below in parentheses after each compound). These include amphipathic anti-tumor compounds such as the plant alkaloids vincristine (1.4 mg/m$^2$), vinblastine (4–18 mg/m$^2$) and etoposide (35–100 mg/m$^2$), and the anthracycline antibiotics including doxorubicin (60–75 mg/m$^2$), epirubicin (60–120 mg/m$^2$) and daunorubicin (25–45 mg/m$^2$). The water-soluble anti-metabolites such as methotrexate (3 mg/$^2$), cytosine arabinoside (100 mg/m$^2$), and fluorouracil (10–15 mg/kg), the antibiotics such as bleomycin (10–20 units/$^2$), mitomycin (20 mg/$^2$), plicamycin (25–30 µg/m$^2$) and dactinomycin (15 µg/m$^2$), and the alkylating agents including cyclophosphamide (3–25 mg/kg), thiotepa (0.30–0.4 mg/Kg) and BCNU (150–200 mg/m$^2$) are also useful in this context. Also as noted above, the liposomes may contain encapsulated tumor-therapeutic peptides and protein drugs, such as IL-2, and/or TNF, and/or immuno-modulators, such as M-CSF, which are present alone or in combination with anti-tumor drugs, such as an doxorubicin.

In another method of treatment provided by the invention, an antibody modified by a ligand molecule, such as a biotinylated antibody, may be administered parenterally first. After about 24 to 48 hours to permit selective localization of the antibody to a target site, liposomes containing a liposome-entrapped compound, and a surface-bound anti-ligand molecule, such as avidin, are administered parenterally. Liposomes with the surface-bound avidin will be retained at target sites by biotin molecules covalently attached to the antibodies.

To minimize nonspecific binding of liposomes containing the liposome-entrapped compound, multivalent species capable of binding multiple antibodies may be administered between about 24 to 48 hours after administration of the biotinylated antibodies to accelerate clearance of the antibodies from the bloodstream. These multivalent species may be empty liposomes having surface-bound avidin, but not containing the liposome-entrapped compound. The empty liposomes may or may not have a hydrophilic polymer surface layer. Alternatively, the multivalent species may be avidin molecules.

These multivalent species serve to chase nonspecifically-bound biotinylated antibodies from sites in the bloodstream. After the chase, liposomes containing the therapeutic compound in liposome-entrapped form, the surface-bound anti-ligand molecules, such as avidin, and the PEG layer on the liposome surface are administered. Performing the chase with the multivalent species will prevent binding of liposomes containing liposome entrapped-drug at non-specific sites and will maximize the specificity of therapeutic compound targeting in vivo.

It will be appreciated that the present method can be employed for improved targeting of an imaging agent to a tumor, for tumor diagnosis. Here the imaging agent, typically a radioisotope in chelated form, or a paramagnetic molecule, is entrapped in liposomes, which are then administered IV to the subject being examined. After a selected period, typically 24–48 hours, the subject is then monitored, for example by gamma scintillation radiography in the case of the radioisotope, or by nuclear magnetic resonance (NMR) in the case of the paramagnetic agent, to detect regions of local uptake of the imaging agent.

It is also anticipated that long circulating antibody-liposomes would be useful for delivery of anti-infective compounds to regions of infections. Sites of infection, like tumors, often exhibit specific antigens or antigens expressed at higher levels that may be targeted by the antibody-liposome compositions. It is expected that antibody-liposomes containing antibiotics (such as aminoglycosides, cephalosporins, and beta lactams) would improve compound localization at sites of infection, thereby improving the therapeutic index of such agents—particularly ones which exhibit dose-related toxicities, such as the aminoglycosides.

The following examples illustrate, but in no way are intended to limit the present invention.

MATERIALS AND METHODS $IgG_1$ monoclonal antibody 174H.64 (mAb) directed against mammalian squamous carcinoma was a generous gift of Biomira, Inc. (Edmonton, AB). Hydrogenated soy phosphatidylcholine (HSPC) was obtained from Asahi Chemicals, Japan. Cholesterol (CH) was purchased from Sigma Chemicals (St. Louis, Mo.).

EXAMPLE 1

Preparation of DSPE-PEG-Maleimide and Antibody Coupling to DSPE-PEG-Maleimide

A. Preparation of the Mono 2-nitrobenzenesulfonamide of PEG bis(amine) (Compound II)

A mixture of 1.7 g (0.5 mmole) of commercially available polyethylene glycol bis(amine) and 104 mg (0.55 mmole) of 2-nitrobenzene sulfonyl chloride were added to a round bottomed flask. The minimum amount of dioxane to effect solution (about 15 ml) and 280 microliters of triethylamine (2 mmole) were added. The reaction flask was stoppered and let to stand at room temperature for 4 days.

Thin layer chromatography (TLC) on SiO2 coated plates using a solvent mixture of the following composition CHCl3/CH3OH/H2O/NH4OH; 130/70/8/0.5; v/v/v/v showed fluorescence quenching spots at Rf=0.87 to 0.95 and Rf=0.68–0.75. The 2-nitro benzene sulfonyl chloride was a more compact spot at Rf=0.85. The UV absorbing material at Rf=0.87–0.95 probably represented the bis-2-nitro-benzenesulfenamide. The material at Rf=0.68–0.75 probably represented the desired mono-2-nitrobenzenesulfonaimde of the starting diamine.

The solvent was evaporated under vacuum to obtain 2.135 g of a yellow syrup. It was dissolved in 5 ml chloroform and placed at the top of a 21 mm×270 mm column of SiO2 wetted with chloroform. The product was purified by passing through the column, in sequence:

| 100 ml | 100% chloroform | 0% (1% conc. NH$_4$OH in MeOH) |
| 200 ml | 90% chloroform | 10% (1% conc. NH$_4$OH in MeOH) |
| 100 ml | 80% chloroform | 20% (1% conc. NH$_4$OH in MeOH) |
| 100 ml | 70% chloroform | 30% (1% conc. NH$_4$OH in MeOH) |

Fifty ml aliquots were collected separately and assayed by TLC as described above. Most of the yellow, ninhydrin positive-reacting material was eluted in the 20% (1% conc. NH$_4$OH in MeOH) fraction. The fractions were dried and resulted in 397 mg of a bright yellow solid. The yield of the pure sample was about 20%

B. Preparation of the Imidazole Carbamate of the Mono 2-nitrobenzenesulfonamide of PEG bis(amine)(Compound III)

550 mg (0.15 mmole) of the 2-nitrobenzenesulfonamide of PEG bis(amine) were dissolved in anhydrous benzene. To this was added 49 mg of carbonyl diimidazole (0.3 mmole) and 28 microliters (0.20 mmole) of triethylamine. The air in the reaction vessel was displaced with nitrogen, the flask stoppered and heated in an 80 degree oil bath for 4 hours. TLC on silicate-coated plates using the same solvent system as described above, showed that all the starting sulfonamide (Rf=0.72) had been consumed, and had been replaced by an iodine absorbing material at Rf=0.92.

The solvent was removed under vacuum. The residue was dissolved in about 2.5 ml chloroform and transferred to the top of a 21×280 mm column of silicate which was wetted with chloroform. The following solvents were passed through the column, in sequence:

| 100 ml | 100% chloroform | 0% (1% conc. NH$_4$OH in CH$_3$OH) |
| 100 ml | 90% chloroform | 10% (1% conc. NH$_4$OH in CH$_3$OH) |
| 200 ml | 80% chloroform | 20% (1% conc. NH$_4$OH in CH$_3$OH) |

50 ml fractions were collected and assayed by TLC, the desired product was found predominantly in the 20% (1% conc. NH$_4$OH in CH3OH fraction). When the faction was evaporated to dryness, the sample afforded 475 mg of a lemon-yellow solid. This was dissolved in 4.75 ml benzene.

C. Preparation of the DSPE Carbamide of the 2-nitrobenzene Sulfonamide of PEG bis(amine)

To the 450 mg (0.125 mmole) of 2-nitrobenzenesulfonamide of the imidazole carbamide of the PEG bis(amine) dissolved in 4.5 ml benzene was added 93 mg DSPE (0.125 mmole) and 70 microliters (0.50 mmole) of triethylamine. The air was displaced with nitrogen, the flask stoppered and heated in an oil bath at 80 degrees for 6 hours. The flask was cooled to room temperature. DSPE migrates in the above described TLC system with an Rf of 0.54. TLC indicated that all the DSPE had been consumed. The solvent was evaporated under vacuum. The residue was dissolved in 2.5 ml chloroform and placed at the top of a 21×260 mm column of silicate wetted with chloroform. The sample was purified by passing through the column in sequence:

| 100 ml | 100% chloroform | 0% (1% conc. NH$_4$OH in MeOH) |
| 200 ml | 90% chloroform | 10% (1% conc. NH$_4$OH in MeOH) |
| 100 ml | 80% chloroform | 20% (1% conc. NH$_4$OH in MeOH) |
| 100 ml | 70% chloroform | 30% (1% conc. NH$_4$OH in MeOH) |

The desired product eluted at 20% (1% conc. NH$_4$OH in MeOH), was evaporated and afforded 358 mg of a bright yellow solid with an Rf=0.95. Fractions containing imidazole were not used and the final yield of the product (0.0837 mmoles) was 65%.

D. Preparation of the DSPE Carbamide of PEG bis(amine) (Compound IV)

About 358 mg of nitrobenzenesulfenamide of the DSPE carbamate of polyethylene glycol bis (amine) were dissolved in 10 ml ethanol. To the solution were added 2.4 ml water and 1.2 ml acetic acid. The mixture was allowed to stand at room temperature for 18 hours. TLC analysis showed only partial deprotection. Another 2.3 ml water, and another 1.2 ml acetic acid were added and the reaction was left standing overnight. On silicate coated plates, using a similar solvent system as described above as the developer, fluorescence quenching material appeared at Rf=0.86 and Rf=0.74. The desired ninhydrin reactive, phosphate containing material migrated with an Rf value of 0.637. This spot showed no fluorescence quenching.

The solvent was removed under vacuum. The residue was redissolved in 15 ml chloroform and extracted with 15 ml 5% sodium carbonate. The mixture was centrifuged to effect separation, and the sodium carbonate phase was reextracted 2× with 15 ml chloroform. The combined chloroform extracts were evaporated under reduced pressure to obtain 386 mg of wax. TLC indicated that the wax was largely a ninhydrin positive, phosphate containing lipid of Rf=0.72.

The wax was dissolved in 2.5 ml chloroform and placed on a silicate column which had been wetted with chloroform. The following solvents were passed through the column in sequence:

| 100 ml of 100% chloroform | 0% (1% CONC. NH₄OH in methanol) |
|---|---|
| 100 ml 90% | 10% |
| 100 ml 80% | 20% |
| 100 ml 70% | 30% |
| 100 ml 50% | 50% |
| 100 ml 0% | 100% |

The samples were assayed by TLC. The desired product was found in the fractions with 30% and 50% (1% conc. NH₄OH in methanol). These samples were combined and evaporated to dryness under vacuum to afford 91 mg (22 micromoles) of a viscous syrup, which corresponded to about 100% conversion.

E. Preparation of the Maleic Acid Derivative of the DSPE Carbamide of PEG bis(amine) (Compound V)

To 18 micromoles of the DSPE carbamide of PEG bis (amine) described above, dissolved in 1.8 ml chloroform, was added 3.5 mg (36 micromoles) maleic anhydride and 5 microliters (36 micromoles) triethylamine. The stoppered flask was allowed to stand at room temperature for 24 hours. The solvent was evaporated. TLC on silicate plates indicated that all the starting material, had been replaced by a ninhydrin negative, phosphate containing material of Rf=0.79–1.00.

F. Preparation of the Maleimide of the DSPE Carbamide of PEG bis (amine) (Compound VI)

The syrup was dissolved in 2 mls acetic anhydride saturated with anhydrous sodium acetate. The solution was heated in a 50 degree oil bath for two hours. 10 ml ethanol were added and evaporated under vacuum. This step was repeated twice to remove excess acetic anhydride and acetic acid. Took up the residue in 1 ml chloroform, and passed the sample through a column with the following solvents in sequence:

| 100 ml | 100% chloroform | 0% (1% conc. NH₄OH in MeOH) |
|---|---|---|
| 200 ml | 90% chloroform | 10% (1% conc. NH₄OH in MeOH) |
| 100 ml | 80% chloroform | 20% (1% conc. NH₄OH in MeOH) |
| 100 ml | 70% chloroform | 30% (1% conc. NH₄OH in MeOH) |

50 ml samples were collected, and the main product was found in the fractions eluted with 10% of 1% conc. NH₄OH in MeOH. The fractions were combined and then evaporated to dryness under vacuum which afforded 52 mg of a pale, yellow, viscous oil, which by TLC migrated with an Rf of 0.98 and contained phosphate. 12.3 mmoles product were obtained which corresponded to a yield of about 34%.

G. Antibody Coupling to the Maleimide Group of PEG

Coupling reactions were performed by adding antibody solution to the liposomes (final protein concentration=0.5 mg/ml) in phosphate buffered saline and incubating the suspension overnight at ambient temperature with gentle shaking at pH 8 under reducing conditions.

EXAMPLE 2

Biodistribution of Antibody-Liposomes

The biodistribution of liposomes containing surface-bound antibodies was compared to that of liposomes lacking surface-bound antibodies. The antibody-liposomes were composed of HSPC:CH:PEG hydrazide, at 2:1:0.1 molar and sheep IgG covalently linked to PEG chain. Liposomes lacking surface-bound antigens were liposomes composed of HSPC:CH:PEG at a 2:1:0.1 molar and liposomes composed of HSPC:CH:PEG hydrazide. The average diameter of the liposomes was between 110 and 120 nanometers. For biodistribution studies the liposomes contained $^{125}$I-tyraminylinulin in liposome-entrapped form.

The antibody-liposomes were prepared as described. A 10 mg/ml solution of IgG was prepared in 100 mM sodium acetate, 70 mMNaCl pH 5.5. For 1 ml of the protein solution, 55 microliters of 0.2M sodium periodate was added. Oxidation proceeded for 1 hour at room temperature. The periodate-treated protein was added to liposomes containing DSPE-PEG hydrazide and incubated overnight at 4° C. Liposomes were separated from free protein by chromatography on Sepharose CL-4B in TES-buffered saline, pH 7.4.

Female CD(ICR) BR (outbred) mice in the weight range of 23–30 grams were obtained from Charles River Canada (St. Constant, QUE), and maintained in standard housing. Mice (three per group) were given a single bolus injection with 0.2 ml of liposomes containing approximately $10^6$ 125I-Tl cpm and 0.5 micromole phospholipid, and approximately 10 micrograms antibody, where applicable. Some groups of mice received injection of free radiolabelled TL. Injections were performed by intravenous injection via the tail vein. After specified periods of time, animals were anesthetized with halothane (M.T.C. Pharmaceutical, Ontario) and sacrificed by cervical dislocation. Samples of blood (0.1 ml) and internal organs (liver, spleen, lung, heart, and carcass, which was the remainder of the animal) were collected, tissues were washed and blotted dry to remove superficial blood and counted for label in a Beckman 8000 gamma counter. Blood correction factors, having previously been determined from $^{111}$In-labelled red blood cells (Allen, 1989a), were applied to tissue and carcass.

Data is presented as % of in vivo cpm, which represents the % of counts remaining in the body at a given time point. This corrects for leakage of the label from the liposomes and represents intact liposomes remaining in the body.

TABLE 1

| Liposome Composition (time post-injection) | % of in vivo cpm | | | | | |
|---|---|---|---|---|---|---|
| | Blood | Liver | Spleen | Lung | Heart | Carcass |
| | 2 hours | | | | | |
| HSPC:CH:PEG | 78.1 ± 4.4 | 6.3 ± 0.6 | 2.5 ± 0.4 | 0.1 ± 0.1 | 0.3 ± 0.1 | 11.1 ± 3.8 |
| HSPC:CH:PEG-HZ | 65.6 ± 5.7 | 12.2 ± 1.9 | 1.6 ± 0.2 | 0.4 ± 0.2 | 0.3 ± 0.1 | 18.6 ± 4.2 |
| HSPC:CH:PEG-HZ:IgG | 73.2 ± 6.3 | 10.9 ± 4.4 | 1.0 ± 0.5 | 0.5 ± 0.1 | 0.3 ± 0.1 | 13.0 ± 4.0 |

TABLE 1-continued

| Liposome Composition (time post-injection) | % of in vivo cpm | | | | | |
|---|---|---|---|---|---|---|
| | Blood | Liver | Spleen | Lung | Heart | Carcass |
| 24 hours | | | | | | |
| HSPC:CH:PEG | 26.7 ± 1.1 | 26.4 ± 2.9 | 5.1 ± 0.5 | 0.4 ± 0.1 | 0.5 ± 0.0 | 38.3 ± 2.2 |
| HSPC:CH:PEG-HZ | 14.0 ± 2.3 | 34.8 ± 2.1 | 3.8 ± 0.8 | 0.4 ± 0.2 | 0.4 ± 0.0 | 42.4 ± 4.5 |
| HSPC:CH:PEG-HZ:IgG | 23.1 ± 3.3 | 27.5 ± 4.2 | 3.4 ± 0.5 | 0.3 ± 0.1 | 0.3 ± 0.1 | 38.7 ± 1.8 |

As shown in Table 1 the biodistribution of liposomes containing antibody covalently attached to the end of a PEG chain by a hydrazide group are very similar to those of liposomes containing nonfunctionalized PEG chains. Liposome biodistribution was determined for the blood, liver, spleen, lung, heart and carcass.

EXAMPLE 3

Preparing Liposomes with Coupled Biotinylated Antibodies

Liposomes were composed of hydrogenated soy phosphatidylcholine:cholesterol:polyethylene glycol-distearolyphosphatidyl-ethanolamine (HSPC:CH:PEG-DSPE), 2:1:0.1 molar ratio, extruded to an average diameter of 112 nm (range 98 to 116). Liposomes for monoclonal antibody attachment were composed of hydrogenated soy phosphatidylcholine:cholesterol:polyethylene glycol-distearylphosphatidyl-ethanolamine (HSPC:CH:PEG-DSPE), 2:1:0.1 molar ratio, and 0.05 mole percent biotin-PE, extruded to an average diameter of 112 nm (range 98 to 116).

Antibody, 5 mg IgG (174H.64 mAb), in 1 ml sodium borate buffer (0.1M, pH 8.8), is incubated with 100 microliters N-hydroxysuccinimide biotin (10 mg/ml in dimethyl sulfoxide) at room temperature for four hours. Free biotin was removed from biotinylated antibodies by passage through a Sephadex G-25 column (25×1 cm) in TES buffered saline.

Avidin-coated liposomes, prepared by incubating biotinylated liposomes with avidin are incubated with biotinylated antibodies for 30 minutes. Liposome bound antibody is separated from free antibody on a Sepharose CL-4B column (40×1 cm) in TES-buffered saline.

The procedure did not change the size of the liposomes or result in liposome aggregation. The liposomes were injected at a phospholipid dose of 1.2–1.4 µmol/mouse and a mAb 174H.64 dose, where applicable, of 10.5–12.5 µg/mouse. DOX was encapsulated by a remote loading method previously described (Mayer).

EXAMPLE 4

Deoxyuridine Uptake and In vivo Survival Experiments

A. Deoxyuridine Uptake

DBA2 mice (Jackson Laboratories) were injected i.v. with $2 \times 10^5$ KLN-205 cells. At 3 days post-injection of KLN-205 cells, the mice were injected i.v. with single injections of either 0.2 ml phosphate-buffered saline (PBS) (untreated controls) or with 6 mg/kg of either free DOX, 6 mg/kg of DOX entrapped in HSPC:CH:PEG-DSPE liposomes (liposomal DOX), 6 mg/kg of DOX entrapped in HSPC:CH:PEG-DSPE liposomes containing attached antibody 174H.64 (mAb-liposomal DOX) or mAb-liposomes (11–39 µg mAb) lacking DOX, all in 0.2 ml of sterile saline.

On the 45th day after injection, mice were injected with 2 µCi each of $^{125}$I-dUrd and 4 hr later the lungs were removed, cut into small pieces, washed with 10% trichloroacetic acid and counted in a gamma counter.

B. In vivo Survival Experiments

For in vivo survival experiments the injection protocols were identical to above, except the survival of the mice was monitored daily until evidence of morbidity resulted in their termination, at which point gross pathological examination of their internal organs for the presence of tumor nodules was performed.

Two long-term survivors were sacrificed on day 170 and showed no evidence of tumor.

EXAMPLE 5

Histopathology

Mice were injected with $2 \times 10^5$ KLN-205 cells and 3 days post-injection of tumor were treated with single i.v. injections of 6 mg/kg free DOX, liposomal DOX or mAb-liposomal DOX as in the previous section. On day 45, lungs were removed from the different treatment groups. Tumor masses were randomly located throughout all lung fields and mid-sagittal sections were made from each of the largest lung lobes. The right and left caudal lobes were fixed in 10% neutral buffered formalin, processed into paraffin blocks, sectioned at 5 µm and stained with haematoxylon and eosin.

Histopathological slides were prepared from normal lung, untreated lung, lung from mice treated with free DOX, lung from mice treated with liposomal DOX, lung from mice treated with mAb-liposomal DOX. Animals that received single injections of mAb liposomal DOX showed no evidence of tumor nodules compared to animals that had received any of the other doxorubicin treatments.

Table 2 shows the number and diameter of discrete tumor nodules per linear cm of lung right and left caudal lobes, in mid-sagittal sections stained with haematoxylon and eosin. The lungs of all animal within each experimental group appear similar upon gross inspection and measurements were made for 1 typical animal from each group of 5 animals examined, except in the case of mAb-liposomal DOX where numbers were determined from 2 typical animals.

TABLE 2

| Treatment group | Left lung | | Right lung | |
| --- | --- | --- | --- | --- |
| | # of foci | diameter mm ± S.D. | # of foci | diameter mm ± S.D. |
| Normal (control) | 0 | — | 0 | — |
| Untreated (control) | 28 | 0.43 ± 0.18 | 34 | 0.41 ± 0.19 |
| Free DOX | 40 | 0.43 ± 0.18 | 23 | 0.36 ± 0.21 |
| Liposomal DOX | 10 | 0.31 ± 0.06 | 19 | 0.39 ± 0.23 |
| mAb-liposomal DOX | 0.3 | 0.22 | 0.7 | 0.18, 0.26 |

EXAMPLE 6

Liposome Uptake into Lung

Uptake of liposomes labelled with $^{125}$I-tyraminylinulin ($^{125}$I-TI) into lung in DBA/2 mice (3/group) at 15 minutes post-injection was determined. Uptake experiments provide a measure of uptake of intact liposomes. Liposome uptake was examined at 3 days and 45 days after i.v. injection of $2 \times 10^5$ KLN-205 cells. Experimental groups were composed of tumor-free (control) animals receiving either HSPC:CH:PEG-DSPE or mAb-HSPC:CH:PEG-DSPE liposomes (2:1:0.1 molar ratio, no drug), or tumor-bearing animals receiving similar liposomes.

Liposome uptake experiments were performed to confirm specific localization of the liposomes to the lungs. The uptake of liposomes and mAb-liposomes into lung in tumor bearing mice at 3 days post-injection was 29.4±4.1 and 72.7±26.9 cpm/mg total lung tissue, respectively. This compares with 27.4±10.6 and 41.6±29.6 cpm/mg total lung tissue for tumor-free lungs.

At 45 days post-injection the uptake of mAb liposomes was 121.9±35.4, as compared with tumor-free mice (42.9±6.2 cpm/mg total lung tissue). Lung uptake at 45 days post-injection of tumor was 5.0±1.1% of in vivo mAb liposomes for tumor-bearing mice compared to 1.3 ±0.2% for tumor-free mice at 24 hours post-injection of liposomes. The increased uptake of mAb liposomes suggests that they are able to bind to proliferating tumor cells localized in the lung.

While the invention has been described with reference to specific methods and embodiments, it will be appreciated that various modifications and changes may be made without departing from the invention.

It is claimed:

1. A method of administering an anti-tumor compound to a subject, for solid tumor treatment, comprising administering to the subject, by parenteral injection, liposomes having sizes in the range of 0.05 to 0.12 microns, and containing an anti-tumor compound in liposome-entrapped form, a surface coating of polyethylene glycol chains at a surface concentration thereof sufficient to extend the blood circulation time of the liposomes severalfold over that of liposomes in the absence of such coating, and antibodies or antibody fragments effective to bind specifically to tumor-associated antigens, wherein the polyethylene glycol chains contain, in a portion thereof, functionalized reactive groups at their free ends to which said antibodies or antibody fragments are covalently attached.

2. The method of claim 1, wherein said tumor cells are squamous carcinoma cells localized in the lung.

* * * * *